(12) United States Patent
Hossainy

(10) Patent No.: US 7,511,103 B2
(45) Date of Patent: Mar. 31, 2009

(54) POLY(ESTER AMIDE) BLOCK COPOLYMERS

(75) Inventor: Syed Faiyaz Ahmed Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/186,415

(22) Filed: Aug. 5, 2008

(65) Prior Publication Data

US 2008/0293893 A1  Nov. 27, 2008

Related U.S. Application Data

(62) Division of application No. 11/023,837, filed on Dec. 27, 2004, now Pat. No. 7,419,504.

(51) Int. Cl.
*C08G 69/00* (2006.01)
*C08G 69/44* (2006.01)

(52) U.S. Cl. .............. 525/411; 525/415; 525/420; 525/425; 525/432; 525/434

(58) Field of Classification Search .......... 528/271, 528/272; 525/411, 415, 420, 425, 432, 434
See application file for complete search history.

(56) References Cited

U.S. PATENT DOCUMENTS

| 6,365,172 | B1 * | 4/2002 | Barrows | 424/423 |
| 6,503,538 | B1 * | 1/2003 | Chu et al. | 424/497 |
| 6,511,748 | B1 * | 1/2003 | Barrows | 428/373 |

* cited by examiner

*Primary Examiner*—Ana L Woodward
(74) *Attorney, Agent, or Firm*—Squire Sanders & Dempsey LLP

(57) ABSTRACT

Provided herein is a copolymer that includes a soft block (A) and a hard block (B) comprising a tyrosine di-peptide. The copolymer can be any of AB, ABA or BAB type block copolymers. The soft block can include a PEA polymer.

5 Claims, No Drawings

POLY(ESTER AMIDE) BLOCK COPOLYMERS

CROSS-REFERENCE TO RELATED APPLICATION

This is a divisional application of U.S. application Ser. No. 11/023,837, filed Dec. 27, 2004 now U.S. Pat. No. 7,419,504, the teaching of which is incorporated herein in its entirety by reference.

BACKGROUND OF THE INVENTION

1. Field of the Invention

This invention generally relates to poly(ester amide) block copolymers useful for forming a bioabsorbable device such as a stent or for coating an implantable device such as a drug-delivery stent.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain vascular patency.

Stents are used not only as a mechanical intervention but also as a vehicle for providing pharmacological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Pharmacological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent.

Accordingly, there is a need to have stent coatings with improved biological compatibility and improved mechanical properties.

The embodiments of the present invention provide for polymers and combination of polymers for coating stents and other implantable medical devices, where the polymers forming the coatings are biologically compatible and absorbable.

SUMMARY OF THE INVENTION

In an aspect of the present invention, provided herein is a copolymer that includes a soft block (A) which can be a poly(ester amide) (PEA) block (A) and another block (B). The copolymer can be any of AB, ABA, and BAB type block copolymer. By varying the relative amount of the soft block (e.g. PEA block) and the hard block, one can obtain a copolymer with a $T_g$ for mechanical integrity in drug-delivery stent applications.

The copolymer can be used alone or optionally in combination with a biobeneficial material and/or a biocompatible polymer to form a coating on an implantable device or to form the implantable device itself. When the copolymer is used in combination with a biobeneficial material, the copolymer and the biobeneficial material can be co-deposited or applied in sequence during the coating process.

DETAILED DESCRIPTION

Poly(ester amide) Block Copolymer

In one aspect of the present invention, provided herein is a copolymer that includes a soft block which can be a poly(ester amide) (PEA) block (A) and a hard block (B) derived from a biocompatible polymer. The copolymer can be any of AB, ABA, and BAB type block copolymer. By varying the relative amount of the soft block (e.g., a PEA block) and the hard block, one can obtain a copolymer with a glass transition temperature ($T_g$) for mechanical integrity in drug-delivery stent applications.

The terms "hard" and "soft" are relative terms and, as used herein, refer to mechanical strength and toughness of the block copolymer defined herein. The term "hard block" refers to the block that has a higher mechanical strength and toughness whereas the term "soft block" refers to the block that has a lower mechanical strength and toughness. Generally, the hard block in a block copolymer has a glass $T_g$ higher than the $T_g$ of the soft block. However, the hard block in a block copolymer described herein may sometimes have a $T_g$ approximately the same as or lower than the $T_g$ of a soft block.

The copolymer can be used alone or optionally in combination with a biobeneficial material and/or a biocompatible polymer to form a coating on an implantable device or to form the implantable device itself. When the copolymer is used in combination with a biobeneficial material, the copolymer and the biobeneficial material can be co-deposited or applied in sequence during the coating process.

The implantable device or the coating may also include a bioactive agent. Exemplary bioactive agents include, but are not limited to, paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, prodrugs thereof, co-drugs thereof, and combinations thereof. The implantable device can be implanted in a patient to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

A. Poly(ester amide) Block (A)

Poly(ester amide), as used herein, encompasses any polymer having both ester and amide groups in its backbone. In one embodiment, the PEA is formed of a diacid and another moiety having both amino and hydroxyl functionalities. One of such PEA is described in, e.g., U.S. Pat. No. 6,503,538, B1. The diacid is preferably a C2-C12 diacid, aliphatic or with unsaturation. The amino acid can be, for example, glycine, valine, alanine, proline, glutamine, methionine, leucine, isoleucine, or phenylalanine. An optional second amino acid may be included. The second amino acid can be, for example, lysine, tyrosine, tryptophan, arginine, histidine, glutamic acid, aspartic acid, threonine, serine, or cysteine. The second amino acid may contain a side group to enable the attachment of pharmacologically active compounds or property modifiers. PEA polymers with various thermal properties can be readily prepared by varying these components during synthesis.

PEA can be made by condensation polymerization utilizing, among others, diamino subunits and dicarboxylic acids (Scheme I). In Scheme I, the dicarboxylic acids are converted to an active di-p-nitrophenyl derivative. As shown in Scheme I, when the dicarboxylic acid and the diamino subunits are used stoichiometrically, the PEA formed would have one terminal carboxylic acid group and one amino group. When the dicarboxylic acid and the diamino subunits are not used at a ratio of 1:1, the PEA thus formed can have end groups in favor of the carboxylic acid group, if the dicarboxylic acid subunit is used more than the diamino subunit, or in favor of the amino group, if the diamino subunit is used more than the dicarboxylic acid subunit. Accordingly, the PEA molecule would have reactive carboxylic acid or amino end groups.

The soft block can also be derived from PEA having another moiety attached thereto, e.g., poly(ethylene glycol) (PEG), 4-amino-2,2,6,6-tetramethylpiperidine-1-oxyl (4-amino-TEMPO), or a combination thereof. In some embodiments, the soft block can be PEA, PEA-PEG, PEA-4-amino-TEMPO, PEG, or a combination thereof.

B. Hard Block (B)

The hard blocks of the PEA block copolymer can be formed of a material having a higher $T_g$ than PEA. In some embodiments, the material is one or more biocompatible polymer. Exemplary biocompatible polymers include, but are not limited to, poly(D,L-lactic acid) (PDLLA, polyglycolic acid (PGA), poly(D,L-lactic acid-co-glycolic acid) (PDLLG), glycerol-sebacic acid, polytyrosine carbonate, polytyrosine, tyrosine oligomer, or tyrosine di-peptide, poly (3-hydroxybutyrate) (PHB), poly(3-hydroxybutyrate-co-3-hydroxyvalerate) (PHBV), poly(3-hydroxyvalerate) (PHV), polyphosphazene, or combinations thereof. The polymer forming the hard block may also include functional groups such as OH, $NH_2$, COOH, SH, positive or negative charge, $SO_3H$, $SO_4H$, halo groups or PEG.

In some embodiments, the hard block is a tyrosine di-peptide. An exemplary tyrosine di-peptide block has a structure of

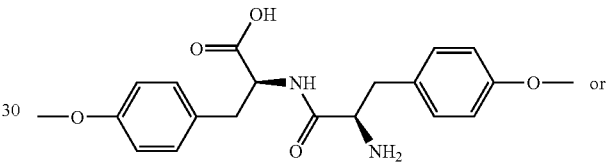 or

Scheme I

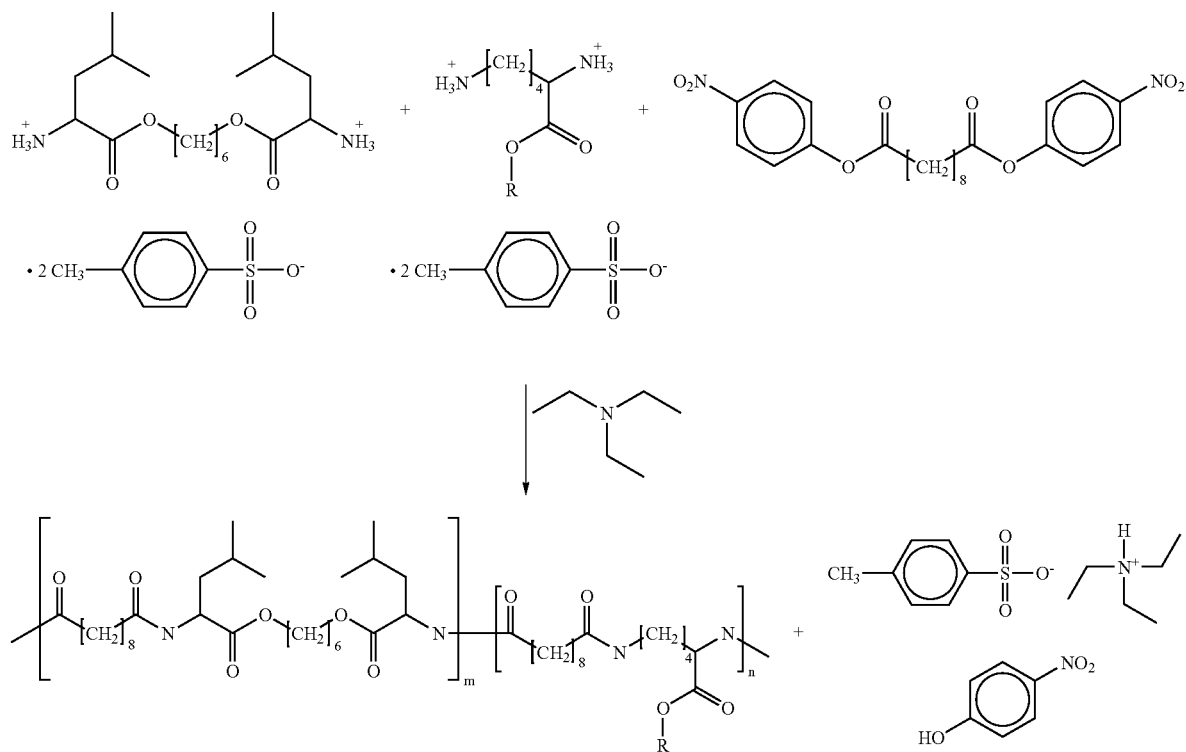

-continued

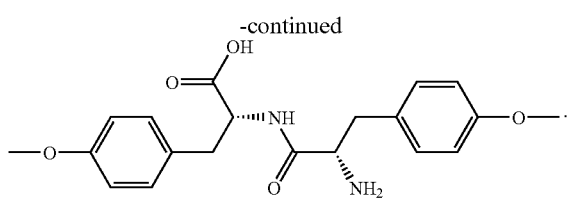

In some embodiments, the tyrosine di-peptide block can be formed of racemic tyrosine. This di-peptide structure is relatively rigid and can increase the $T_g$ and the tensile modulus of the copolymer. In addition, the carboxyl group and the primary amine group on the block can conjugate other reactive moieties such as —COOH, —NH$_2$, aldehyde, keto, hydroxyl, thiol, acyl, and other moieties so as to allow the attachment of functional molecules such as a drug molecule for forming a prodrug, heparin for imparting anti-thrombonic properties to the copolymer, iodo or bromo containing molecules for imparting radioopacity to the copolymer, and other marker compounds for diagnostic uses. The chemistry of forming a prodrug via an ester group, a Schiff base group or other groups that can release the drug molecule under in vivo conditions is described in U.S. application Ser. No. 10/871,658. The chemistry of attaching heparin to a polymer is described in U.S. application Ser. No. 10/857,141. The teachings of both U.S. application Ser. Nos. 10/871,658 and 10/871,658 are incorporated herein by reference.

In some embodiments, the iodo or bromo compound can have a general formula X—Ar—R where X is I or Br and R is a reactive moiety. For example, the iodo or bromo compound can have a structure of

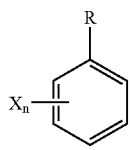

where X can be (1) an organic group $R_1$, provided that $R_1$ has one or more halo groups such as iodo or bromo groups, (2) halo groups such as iodo or bromo groups, or (3) combinations thereof, where R and $R_1$ taken independently can be any chemical grouping having one or more reactive groups capable of conjugating to the carboxyl group or amino group of the tyrosine di-peptide block, which can be, for example, carboxyl groups, aldehyde groups, ester, amino groups, alcohol, thiol, PEG, a leaving group such as tosylate or mesylate, and where n is a positive integer such as 1, 2, or 3.

The tyrosine di-peptide block can be any structural derivative of the tyrosine di-peptide. For example, the tyrosine di-peptide can be desamine tyrosyl-tyrosine di-peptide, desamino tyrosyl-tyrosine hexyl ester (DTH), desamino tyrosyl-tyrosine palmityl ester (DTP), n-benzyloxycarbonyl-tyrosyl-tyrosine hexyl ester (z-TTH), or combinations thereof. Other tyrosine di-peptides are provided in Biomedical Polymers: Designed-to-degrade Systems, Shalaby W. Shalaby (Editor), 1994. Note, in z-TTH, the benzoyl protected group can be reacted to conjugate biobeneficial moieties.

In some embodiments, the tyrosine di-peptide can be randomly incorporated into a PEA polymer. The NH$_2$ and/or COOH groups on the tyrosine di-peptide can be used to conjugate the bromo or iodo compound, a biobeneficial moiety, and/or a bioactive agent described herein.

Biocompatible Polymer

The PEA block copolymer described herein can be used alone or in combination with a biocompatible polymer, optionally with biobeneficial material and/or a bioactive agent to form a bioabsorbable device such as stent or a coating on an implantable device such as a stent. The biocompatible polymer can be any biocompatible polymer known in the art, which can be biodegradable or nondegradable. Representative examples of polymers that can be used to coat an implantable device in accordance with the present invention include, but are not limited to, poly(ester amide), ethylene vinyl alcohol copolymer (commonly known by the generic name EVOH or by the trade name EVAL), poly(3-hydroxyvalerate), poly(L-lactic acid), polycaprolactone, poly(lactide-co-glycolide), poly(3-hydroxybutyrate), poly(3-hydroxybutyrate-co-3-hydroxyvalerate), polydioxanone, polyorthoester, polyanhydride, poly(glycolic acid), poly(D,L-lactic acid), poly(D,L-lactide-co-glycolide) (PDLLAGA), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alpha-olefin copolymers, acrylic polymers and copolymers, vinyl halide polymers and copolymers, such as polyvinyl chloride, polyvinyl ethers, such as polyvinyl methyl ether; polyvinylidene halides, such as vinylidene fluoride based home or copolymer under the trade name Solef™ or Kynar™, for example, polyvinylidene fluoride (PVDF) or poly(vinylidene-co-hexafluoropropylene) (PVDF-co-HFP) and polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, or combinations thereof.

The biocompatible polymer can provide a controlled release of a bioactive agent, if included in the coating and/or if binding the bioactive agent to a substrate, which can be the surface of an implantable device or a coating thereon. Controlled release and delivery of bioactive agent using a polymeric carrier has been extensively researched in the past several decades (see, for example, Mathiowitz, Ed., Encyclopedia of Controlled Drug Delivery, C.H.I.P.S., 1999). For example, PLA based drug delivery systems have provided controlled release of many therapeutic drugs with various degrees of success (see, for example, U.S. Pat. No. 5,861,387 to Labrie, et al.). The release rate of the bioactive agent can be controlled by, for example, selection of a particular type of biocompatible polymer, which can provide a desired release profile of the bioactive agent. The release profile of the bioactive agent can be further controlled by selecting the molecular weight of the biocompatible polymer and/or the ratio of the biocompatible polymer to the bioactive agent. One of ordinary skill in the art can readily select a carrier system using a biocompatible polymer to provide a controlled release of the bioactive agent.

A preferred biocompatible polymer is a polyester, such as one of PLA, PLGA, PGA, PHA, poly(3-hydroxybutyrate) (PHB), poly(3-hydroxybutyrate-co-3-hydroxyvalerate), poly((3-hydroxyvalerate), poly(3-hydroxyhexanoate), poly(4-hydroxybutyrate), poly(4-hydroxyvalerate), poly(4-hydroxyhexanoate), and a combination thereof, and polycaprolactone (PCL).

Bioactive Agents

The PEA copolymers disclosed herein can form a coating or a bioabsorbable device such as a bioabsorbable stent with one or more bioactive agents. These bioactive agents can be any therapeutic, prophylactic, or diagnostic agents. These agents can have anti-proliferative or anti-inflammatory properties or can have other properties such as antineoplastic, antiplatelet, anti-coagulant, anti-fibrin, antithrombonic, antimitotic, antibiotic, antiallergic, antioxidant as well as cytostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy) ethyl-rapamycin (everolimus), and its functional or structural derivatives, paclitaxel and its functional and structural derivatives. Examples of rapamycin derivatives include methyl rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, bioactive RGD, and genetically engineered epithelial cells. The foregoing substances can also be used in the form of prodrugs or co-drugs thereof. The foregoing substances are listed by way of example and are not meant to be limiting. Other active agents which are currently available or that may be developed in the future are equally applicable.

The dosage or concentration of the bioactive agent should be less than the level at which the bioactive agent produces toxic effects and greater than the level at which non-therapeutic results are obtained. The dosage or concentration of the bioactive agent can depend upon factors such as the particular circumstances of the patient, the nature of the trauma; the nature of the therapy desired, the time over which the ingredient administered resides at the vascular site, and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Method of Use

In accordance with embodiments of the invention, a coating of the various described embodiments can be formed on an implantable device or prosthesis, e.g., a stent. For coatings including one or more active agents, the agent will retain on the medical device such as a stent during delivery and expansion of the device, and released at a desired rate and for a predetermined duration of time at the site of implantation.

Preferably, the medical device is a stent. A stent described herein is useful for a variety of medical procedures, including, by way of example, treatment of obstructions caused by tumors in bile ducts, esophagus, trachea/bronchi and other biological passageways. A stent described herein is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A copolymer comprising a soft block (A) and a hard block (B),
    wherein the soft block comprises poly(ester amide) (PEA), and
    wherein the hard block comprises a tyrosine di-peptide and a polymer selected from the group consisting of poly(D, L-lactic acid-co-glycolic acid) (PDLLG), poly(glycerol-sebacic acid), polytyrosine carbonate, polytyrosine, tyrosine oligomer, poly(3-hydroxybutyrate) (PHB), poly(3-hydroxybutyrate-co-3-hydroxyvalerate) (PHBV), poly(3-hydroxyvalerate) (PHV), polyphosphazene, and combinations thereof.

2. The block copolymer of claim 1, wherein the soft block further comprises poly(ethylene glycol) (PEG).

3. The block copolymer of claim 1 wherein the tyrosine di-peptide forms a tyrosine di-peptide block.

4. The copolymer of claim 3, wherein the tyrosine di-peptide block is

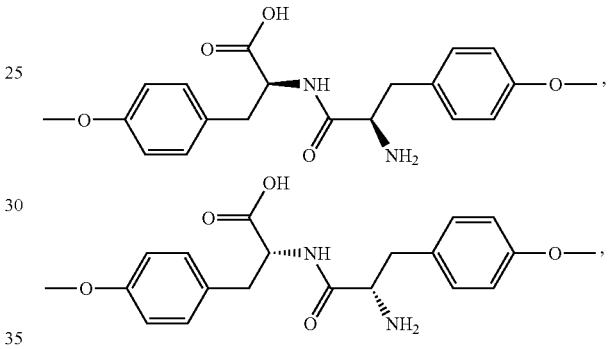

racemic tyrosine di-peptide, desamine tyrosyl tyrosine di-peptide, desamine tyrosyl-tyrosine di-peptide, desamino tyrosyl-tyrosine hexyl ester (DTH), desamino tyrosyl-tyrosine palmityl ester (DTP), n-benzyloxycarbonyl-tyrosyl-tyrosine hexyl ester (z-TTH), or combinations thereof.

5. The polymer of claim 1, which is an AB, ABA or BAB type block copolymer.

* * * * *